(12) United States Patent
Radin et al.

(10) Patent No.: US 9,370,396 B2
(45) Date of Patent: Jun. 21, 2016

(54) TRANSITION APPARATUS FOR USE WITH A MEDICAL DEVICE HAVING AN ELONGATE ELEMENT

(75) Inventors: Andrew M. Radin, Palo Alto, CA (US); Thomas B. Eby, Mountain View, CA (US); Vera S. Boudtchenko, Mountain View, CA (US); Jennifer Teng, Saratoga, CA (US); John P. Goetz, Aptos, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1995 days.

(21) Appl. No.: 11/964,158

(22) Filed: Dec. 26, 2007

(65) Prior Publication Data
US 2009/0171347 A1 Jul. 2, 2009

(51) Int. Cl.
*A61B 18/14* (2006.01)
*A61B 18/00* (2006.01)

(52) U.S. Cl.
CPC ... *A61B 18/1492* (2013.01); *A61B 2018/00363* (2013.01); *A61B 2018/00375* (2013.01); *A61B 2018/00577* (2013.01)

(58) Field of Classification Search
CPC ........ A61B 18/08; A61B 18/10; A61B 18/12; A61B 18/1266; A61B 18/14; A61B 18/1442; A61B 18/1445; A61B 18/1448; A61B 18/1492; A61B 2018/00363; A61B 2018/00375; A61B 2018/00577
USPC ........ 606/27, 41, 42, 45–50, 1; 607/101–102, 607/122; 600/37, 587; 128/898
See application file for complete search history.

(56) References Cited

U.S. PATENT DOCUMENTS

| | | | |
|---|---|---|---|
| 4,204,738 A * | 5/1980 | Tillotson | 439/369 |
| 4,892,520 A | 1/1990 | Gilbaugh | |
| 4,946,440 A | 8/1990 | Hall | |
| 5,152,293 A | 10/1992 | Vonesh et al. | |
| 5,599,333 A * | 2/1997 | Atkinson | 604/326 |
| 5,836,947 A * | 11/1998 | Fleischman et al. | 606/47 |
| 5,916,213 A | 6/1999 | Haissaguerre et al. | |
| 5,921,924 A | 7/1999 | Avitall | |
| 6,142,956 A * | 11/2000 | Kortenbach et al. | 600/564 |
| 6,273,404 B1 * | 8/2001 | Holman et al. | 264/276 |
| 6,314,962 B1 | 11/2001 | Vaska et al. | |
| 6,645,202 B1 | 11/2003 | Pless et al. | |

(Continued)

OTHER PUBLICATIONS

International Search Report and Written Opinion for PCT/US2008/084019 mailed Jan. 26, 2009.

(Continued)

*Primary Examiner* — Michael Peffley
*Assistant Examiner* — Khadijeh Vahdat
(74) *Attorney, Agent, or Firm* — Dykema Gossett PLLC (57) ABSTRACT

A transition apparatus for use with a medical device having an elongate element is disclosed. The apparatus may include a body defining a lumen for housing at least a portion of the elongate element. The body may have a proximal end configured for releasable connection to the medical device and a distal end. The apparatus may further include a connection piece connected to the distal end of the body. The connection piece may have a first opening configured to receive the elongate element from the lumen of the body and a second opening configured to receive the elongate element from the first opening and direct the elongate element toward the body. A method of connecting a transition apparatus to an ablation device having a leash is also disclosed.

17 Claims, 6 Drawing Sheets

(56) References Cited

U.S. PATENT DOCUMENTS

| | | |
|---|---|---|
| 6,689,128 B2 | 2/2004 | Sliwa, Jr. et al. |
| 6,701,931 B2 | 3/2004 | Sliwa, Jr. et al. |
| 6,719,755 B2 | 4/2004 | Sliwa, Jr. et al. |
| 6,752,805 B2 | 6/2004 | Maguire et al. |
| 6,792,306 B2 | 9/2004 | Henley et al. |
| 6,805,128 B1 | 10/2004 | Pless et al. |
| 6,805,129 B1 | 10/2004 | Pless et al. |
| 6,840,936 B2 | 1/2005 | Sliwa, Jr. et al. |
| 6,858,026 B2 | 2/2005 | Sliwa, Jr. et al. |
| 6,971,394 B2 | 12/2005 | Sliwa, Jr. et al. |
| 7,052,493 B2 | 5/2006 | Vaska et al. |
| 2002/0026178 A1* | 2/2002 | Ouchi ............................... 606/1 |
| 2004/0054363 A1* | 3/2004 | Vaska et al. .................... 606/27 |
| 2004/0260281 A1 | 12/2004 | Baxter, III et al. |
| 2005/0033274 A1 | 2/2005 | Pless et al. |
| 2005/0085731 A1 | 4/2005 | Miller et al. |
| 2005/0096650 A1* | 5/2005 | Ouchi ............................. 606/47 |
| 2006/0184167 A1 | 8/2006 | Vaska et al. |
| 2006/0270900 A1* | 11/2006 | Chin et al. .................... 600/104 |
| 2007/0276179 A1 | 11/2007 | Meyer |
| 2007/0293792 A1 | 12/2007 | Sliwa et al. |

OTHER PUBLICATIONS

"Supplementary European Search Report", EP 08863691 Jul. 25, 2012.

\* cited by examiner

TRANSITION APPARATUS FOR USE WITH A MEDICAL DEVICE HAVING AN ELONGATE ELEMENT

BACKGROUND OF THE INVENTION a. Field of the Invention

The instant invention is directed toward a transition apparatus for use with a medical device having an elongate element, including an apparatus that is configured to use the elongate element itself for attachment of at least a portion of the transition apparatus to the medical device.

b. Background Art

In a normal heart, contraction and relaxation of the heart muscle (myocardium) takes place in an organized fashion as electrochemical signals pass sequentially through the myocardium from the sinoatrial (SA) node located in the right atrium to the atrialventricular (AV) node and then along a well defined route which includes the His-Purkinje system into the left and right ventricles. Atrial fibrillation results from disorganized electrical activity in the heart muscle, or myocardium. An increasingly common medical procedure for the treatment of certain types of cardiac arrhythmia and atrial arrhythmia involves the ablation of tissue in the heart to cut off the path for stray or improper electrical signals.

Ablation may be performed either from within the chambers of the heart (endocardial ablation) using endovascular devices (e.g., catheters) introduced through arteries or veins, or from outside the heart (epicardial ablation) using devices introduced into the chest. The ablation devices are used to create elongated transmural lesions—that is, lesions extending through a sufficient thickness of the myocardium to block electrical conduction—which form the boundaries of the conductive corridors in the atrial myocardium. The ablation devices create lesions at particular points in the cardiac tissue by physical contact of the cardiac tissue with an ablation element and the application of energy.

One difficulty in obtaining an adequate ablation lesion is the dynamic movement of the heart, especially when there is an erratic or irregular heart beat. Another difficulty in obtaining an adequate ablation lesion is maintaining sufficiently uniform contact with the cardiac tissue across the length of the ablation element surface. Without sufficiently continuous and uniform contact, the associated ablation lesions may not be adequate.

An epicardial ablation device may be used to create uniform, continuous, linear lesions during cardiac ablation. The device may be positioned securely around a patient's atrium while the ablation elements of the device apply energy (e.g., high intensity focused ultrasound energy) to the targeted tissue. Each ablation element is retained by a cell carrier. Cell carriers located at the distal and proximal end of the device are configured to provide for attachment of at least one elongate element (e.g., leash). The elongate elements may be configured to be tensioned together to generally connect the ends of the device together so that the device may encircle the cardiac tissue to be ablated.

An introducer may be used to position the ablation device. For example, the introducer may be advanced around the pulmonary veins, and the distal end of the ablation device may then be attached to the proximal end of the introducer. The introducer may be pulled further to wrap the ablation device around the pulmonary veins. In a conventional epicardial ablation device, a blunt transition piece (e.g., releasable assembly) made of rigid plastic is connected to the distal end of the ablation device for connection to the proximal end of the introducer. The blunt transition piece may produce drag during introduction of the device into the patient. Furthermore, in conventional epicardial ablation devices, the transition piece may be attached to the device with sutures, requiring the operator of the device (e.g., a surgeon) to cut at least one of the sutures to free the transition piece (with attached introducer) from the device. Finally, the rigid transition piece provides no management of the elongate elements (e.g., leashes), which increases drag during device introduction and may make it difficult for the operator to locate the elongate elements once the device is ready for final placement around the cardiac tissue. Accordingly, many operators of the medical device tie a suture to attach the elongate elements to the introducer to bring the elongate elements at least partially out of the body to ease the step of locating the elongate elements. Operators then have to later remove that added suture to free the elongate elements.

Thus, there remains a need for a transition apparatus for use with a medical device having an elongate element that is configured for ease of connection to the introducer and detachment from the medical device, without increasing drag during medical device introduction and without time-consuming suturing operations to connect the transition apparatus to the medical device.

BRIEF SUMMARY OF THE INVENTION

It is desirable to be able to provide a transition apparatus for use with a medical device having an elongate element that may replace the rigid transition piece of conventional designs in order to reduce drag during introduction of the medical device, allow for connection of the apparatus to the medical device without time-consuming suturing operations, ease removal of the introducer from the medical device, and manage the elongate elements that may be used to connect the ends of the medical device together for forming a substantially complete ring. This is particularly beneficial in the context of a minimally invasive surgical procedure (e.g., a thoracotomy procedure).

A transition apparatus for use with a medical device having an elongate element is disclosed. The apparatus may include a body defining a lumen for housing at least a portion of the elongate element. The body may have a proximal end configured for releasable connection to the medical device and a distal end. The apparatus may further include a connection piece connected to the distal end of the body. The connection piece may have a first opening or receptacle configured to receive the elongate element from the lumen of the body and a second opening or receptacle configured to receive the elongate element from the first opening or receptacle and direct the elongate element toward the body.

A method of connecting a transition apparatus to an ablation device having a leash is also disclosed. The method may include the step of providing a transition apparatus comprising a body defining a lumen for housing at least a portion of the leash. The body may have a proximal end configured for releasable connection to the medical device and a distal end. The apparatus may further include a connection piece connected to the distal end of the body. The connection piece may have a first opening or receptacle configured to receive the leash from the lumen of the body and a second opening or receptacle configured to receive the leash from the first opening or receptacle and direct the leash toward the body. The method may further include the steps of releasably connecting the connection piece to an introducer; releasably connecting the proximal end of the body to the distal end of the ablation device; threading the leash of the ablation device through the first opening or receptacle; and threading the leash of the ablation device through the second opening or receptacle so that the leash is directed back toward the body.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
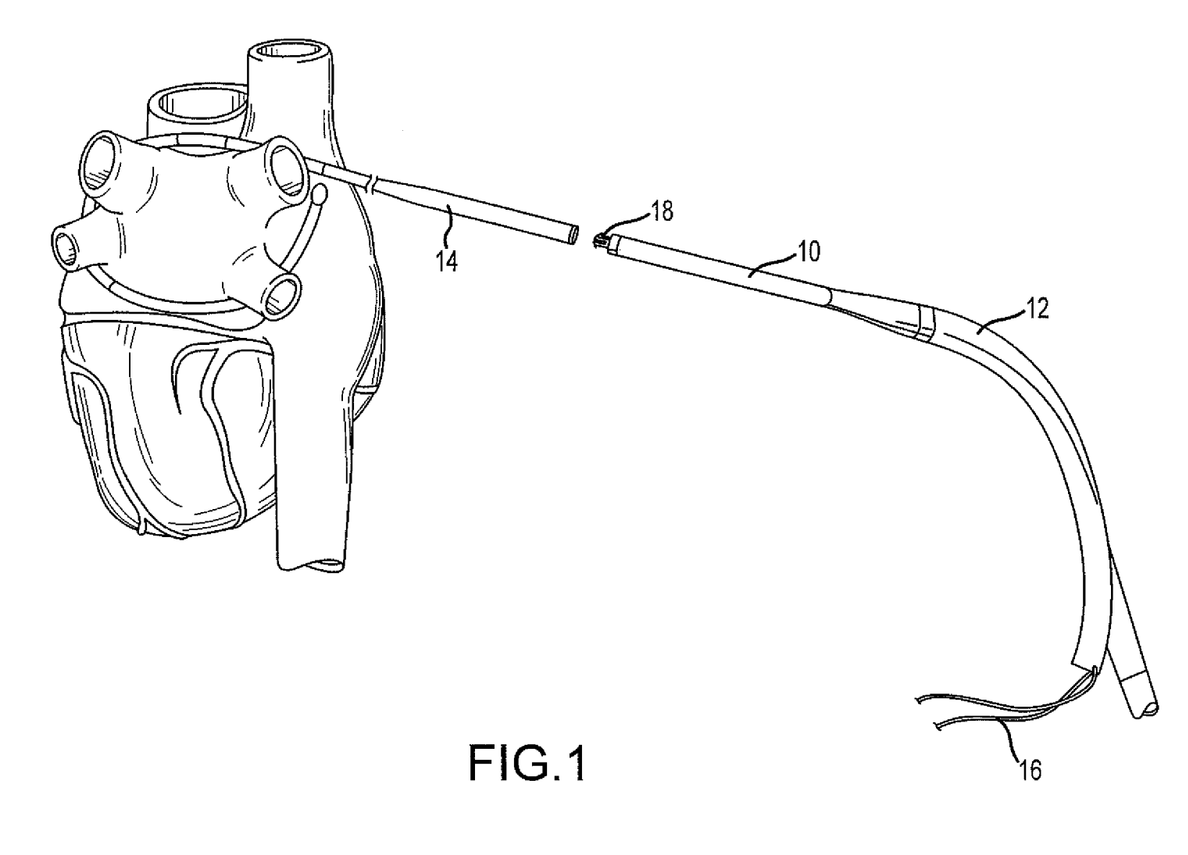
FIG. 1 illustrates a perspective view of a transition apparatus disposed between an ablation device and an introducer.

Referring now to FIG. 1, a transition apparatus 10 for use with a medical device 12 is illustrated. Apparatus 10 may be disposed between medical device 12 and an introducer 14. Medical device 12 may include an elongate element 16.

Device 12 may comprise an epicardial ablation device. Device 12 may comprise a plurality of cells at a first end. Each cell of device 12 may include a cell carrier and an ablation element. Each cell carrier may comprise molded plastic and may include a pair of side walls and an upper wall connected therebetween. A top surface of the upper wall may include one or more protrusions for connection to an electrical cable that may be provided for the supply of energy. A receiving portion located between the side walls of the carrier may be configured to receive at least a portion of an ablation element. The ablation element may comprise an ultrasonic transducer or radio frequency (RF) generator, although various other ablation elements may be used. The ablation element may be provided to transmit energy (e.g., high intensity focused ultrasound energy) to target tissue. A controller may be provided to control delivery of energy.

The cells may be arranged in series and may comprise an assembly. The assembly of cells may be configured to curve and form a substantially complete ring or loop. The assembly of cells may also be configured to form various other shapes. The cells may be positioned adjacent each other so as to promote sufficient movement to allow for shaping of device 12. The ends of device 12 may be connected (e.g., locked) to each other to encircle at least a portion of the heart (e.g., the pulmonary veins) for creating a continuous lesion. Although the device has been described in connection with creating a continuous lesion around the pulmonary veins, the device may also be used for creating other lesions beneficial in treating electrophysiological conditions (e.g., ablating partially around the pulmonary veins or at other locations). The device is not limited to creating lesions completely around the pulmonary veins.

Device 12 may include an elongate element 16 (e.g., leash) at or near at least one end of device 12. Device 12 may include an elongate element 16 at or near both ends of device 12 in an embodiment. Elongate element 16 may comprise braided cable or stainless steel coextruded with a polymer, for example, PEBAX®. Elongate element 16 may include a swage ball as a mechanical means of securing the elongate element 16 to the cell of device 12. If device 12 includes an elongate element 16 at or near both ends of device 12, the elongate element 16 at each end may be tensioned together to generally connect or lock the ends of device 12 together using, for example, tourniquets and suture snares in a manner conventional in the art. Device 12 may have two pairs of opposing elongate elements 16 at one or both ends, but may have any number or configuration of elongate elements 16 in other embodiments. Elongate elements 16 may be, for example, tensioned and cinched together using the tourniquets to approximate the ends of the ablation device 12 so that tensioning the elongate elements 16 forces the ends substantially together. The sizing of the ablation device 12 may provide a snug fit around the pulmonary veins so that tensioning the elongate elements 16 may force the ablation device 12 into contact with the epicardial surface. Hemostats or other suitable devices conventional in the art may be used to pinch or crimp the tourniquet to connect or lock the ablation device 12.

Introducer 14 may be used to place device 12 around a portion of the heart at an epicardial location. For example, introducer 14 may form a substantially closed loop with a small offset near the distal tip and may be advanced around the pulmonary veins. In use, introducer 14 may be passed through an incision in the pericardial reflection adjacent the right superior pulmonary vein adjacent the transverse pericardial sinus. Introducer 14 may then be advanced through the transverse pericardial sinus, around the left superior and inferior pulmonary vein, and out through another incision in the pericardial reflection near the right inferior pulmonary vein.

After introducer 14 is in place around at least a portion of the heart, device 12 may be coupled to the proximal end of introducer 14. As used herein, "proximal" generally refers to a direction away from the body of a patient and toward a clinician. In contrast, "distal" generally refers to a direction toward the body of the patient and away from the clinician. In accordance with an embodiment of the invention, apparatus 10 may be used to connect device 12 to introducer 14. In particular, a distal end of apparatus 10 may be configured for connection to a proximal end of introducer 14. Apparatus 10 may be connected to introducer 14 with any suitable connection, such as a snap-fit connection. In an embodiment, apparatus 10 may include a connection formation or piece 18, and introducer 14 may include a mating part. For example and without limitation, connection piece 18 may comprise a male snap with legs or bayonets, and the mating part on introducer 14 may comprise a female receptacle for the legs or bayonets). In other embodiments, the connection piece on apparatus 10 may include a female receptacle, and introducer 14 may including a male snap with legs or bayonets configured to be disposed in the female receptacle. Connection piece 18 may thus be configured for releasable connection to introducer 14. When device 12 is connected to introducer 14 using transition apparatus 10, device 12 may thus follow the path of introducer 14. As introducer 14 is pulled, device 12 may be wrapped around the pulmonary veins, some other portion of the heart, or some other anatomical structure.

Figure 2:
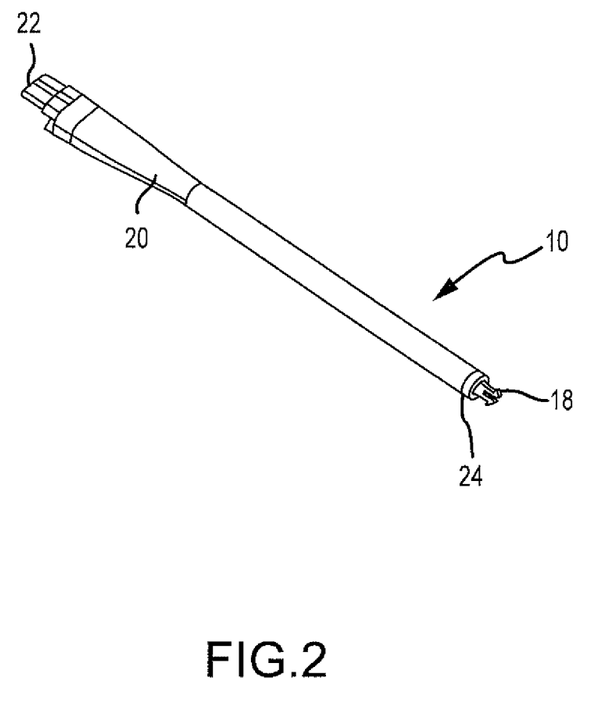
FIG. 2 illustrates a perspective view of the transition apparatus of FIG. 1.

Referring now to FIG. 2, apparatus 10 is illustrated in accordance with an embodiment of the invention. In particular, apparatus 10 may include a body 20. Body 20 may define a lumen for housing at least a portion of elongate element 16 of medical device 12 (e.g., a leash for an epicardial ablation device). Body 20 may be configured to contain at least a portion of elongate element 16 during introduction of device 12 into a body cavity. Accordingly, at least a portion of elongate element 16 may extend through body 20. Management of elongate element 16 may reduce drag and may eliminate the need for operators of device 12 to have to try to later locate elongate elements 16 once device 12 is ready for final positioning around the cardiac tissue. Management of elongate elements 16 may be especially important in medical procedures where an operator of device 12 may have limited access and visibility to the device (e.g., a thoracotomy procedure). Furthermore, because body 20 already provides for management of the elongate elements 16, operators of device 12 may not have to add, and then later remove, a suture to attach the elongate elements 16 to introducer 14 to improve ease of finding the elongate elements, as is often done with conventional designs.

Body 20 may include a proximal end 22 and a distal end 24. Proximal end 22 may be configured for releasable connection to medical device 12 (e.g., a distal end of medical device 12). Distal end 24 of body 20 may be configured to receive connection piece 18. At least a portion of body 20 may be tapered in an embodiment. For example, a portion of body 20 near proximal end 22 may taper to an intermediate location along the length of body 20. The tapered configuration may be provided to reduce drag during introduction of device 12 into a body cavity. The remainder of body 20 may be generally cylindrical in an embodiment and may maintain a constant diameter along the axial length of body 20. Although a cylindrical shape with a constant diameter is mentioned in detail, body 20 may comprise any of various shapes and may have varied diameters along the axial length of body 20 in other embodiments. Body 20 may have a length that is at least about half of the length of elongate element 16. Accordingly, transition apparatus 10 may be configured to manage elongate element 16.

Body 20 may comprise a flexible material. A flexible material may be utilized to further reduce drag during introduction of device 12 into a body cavity through use of transition apparatus 10. The flexible material may comprise any class of thermosets in an embodiment. For example, and without limitation, the flexible material may comprise PEBAX®, PELLETHANE®, or urethanes. Body 20 may be an integrally formed, monolithic structure in an embodiment. In other embodiments, body 20 may comprise one or more separate components that are connected to form body 20.

Figure 3:
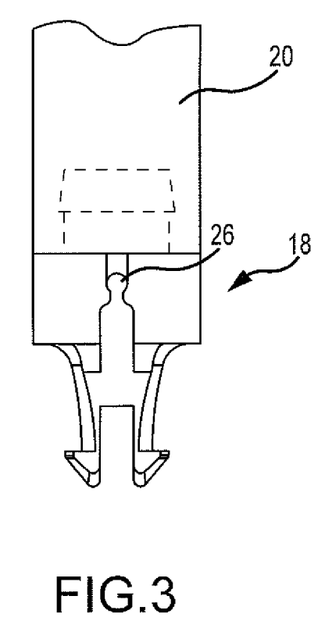
FIG. 3 illustrates a first, partial, side view of the transition apparatus of FIGS. 1-2, including a connection piece in accordance with a first embodiment of the invention.
Figure 4:
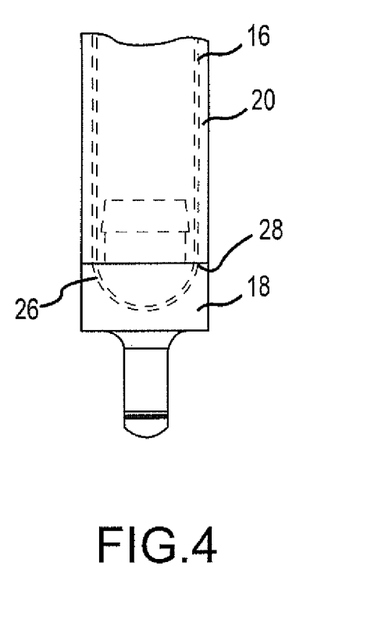
FIG. 4 illustrates a second, partial, side view of the transition apparatus of FIGS. 1-3.
Figure 5:
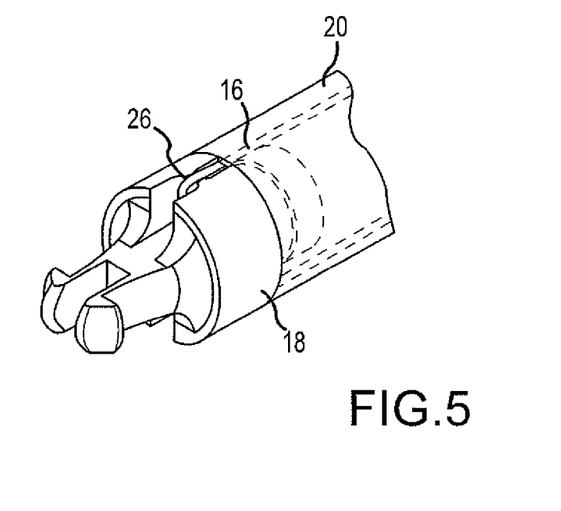
FIG. 5 illustrates a perspective, partial view of the transition apparatus of FIGS. 1-4.

As described above, distal end 24 of body 20 may be configured to receive connection piece 18. Connection piece 18 may be connected (e.g., adhered) to body 20. Referring now to FIG. 3, a first, partial, side view of apparatus 10 including connection piece 18 (e.g., a male snap in the illustrated embodiment) is illustrated. Connection piece 18 may include one or more openings or receptacles for retaining elongate element 16. Referring to FIGS. 3-5, connection piece 18 may include a first opening or receptacle 26. First opening or receptacle 26 may be configured to receive elongate element 16 from the lumen of body 20. Connection piece 18 may further include a second opening or receptacle 28. Second opening or receptacle 28 may be configured to receive elongate element 16 from first opening or receptacle 26 and direct elongate element 16 toward body 20. Accordingly, elongate element 16 may extend from the lumen of body 20 and be received in first opening or receptacle 26. Elongate element 16 may then be looped back through second opening or receptacle 28 and guided back toward the lumen of body 20. At least a portion of elongate element 16 may be exposed outside of connection piece 18 when elongate element 16 is disposed in first and second openings or receptacles 26, 28. Accordingly, a portion of elongate element 16 may be exposed near distal end 24 of body 20. Openings or receptacles 26, 28 may comprise a cut-out, counter-cut groove, and/or an undercut in an embodiment. Openings or receptacles 26, 28 may have other configurations for receiving elongate element 16. Elongate elements 16 may be tensioned and snapped, for example, into openings or receptacles 26, 28. Openings or receptacles 26, 28 may have a smaller diameter than the diameter of elongate element 16, so openings or receptacles 26, 28 may retain elongate elements 16 by squeezing them. Openings or receptacles 26, 28 may thus provide a friction fit for elongate elements 16. In an embodiment, transition apparatus 10 may be connected to medical device 12 only by retention of the elongate element 16 in first and second openings or receptacles 26, 28. Accordingly, transition apparatus 10 may use elongate element 16 itself to connect apparatus 10 to medical device 12. By using elongate element 16 itself, the need for time-consuming suturing operations to attach apparatus 10 to medical device 12 may be eliminated. Transition apparatus 10 may have no other means of connection or attachment to medical device 12, except for the use of elongate element 16, in an embodiment.

Figure 6:
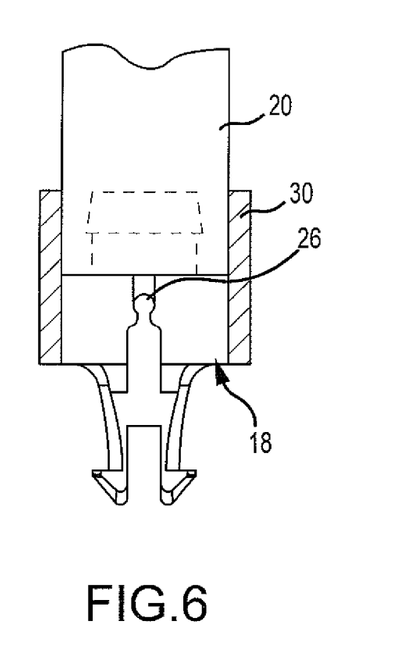
FIG. 6 illustrates a first, partial, side view of the transition apparatus of FIGS. 1-5, including a secondary retention member in accordance with a second embodiment of the invention.
Figure 7:
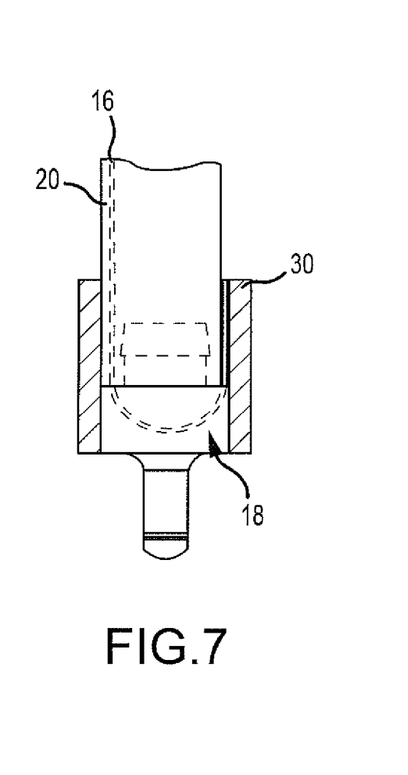
FIG. 7 illustrates a second, partial, side view of the transition apparatus FIG. 6.

Referring now to FIGS. 6-7, transition apparatus 10 may include a secondary retention member 30 in a second embodiment. Secondary retention member 30 may be provided to further retain elongate element 16. Secondary retention member 30 may comprise a means for mechanical or chemical retention. For example, secondary retention member 30 may comprise a tube as illustrated. In other embodiments, secondary retention member 30 may comprise, for example and without limitation, a plastic part, heat shrink tubing, or adhesive tape. Although these exemplary secondary retention members are mentioned in detail, the secondary retention member may comprise other means in other embodiments. Secondary retention member 30 may cover the exposed portions of elongate element 16 that are exposed and outside of connection piece 18. Elongate element 16 may extend to the side of body 20. For example, one of openings or receptacles 26, 28 may comprise a gap between the exterior surface of body 20 and the interior surface of secondary retention member 30. Accordingly, the portion of elongate element 16 exposed outside of the exterior surface of body 20 may be retained by secondary retention member 30 in an embodiment.

Figure 8:
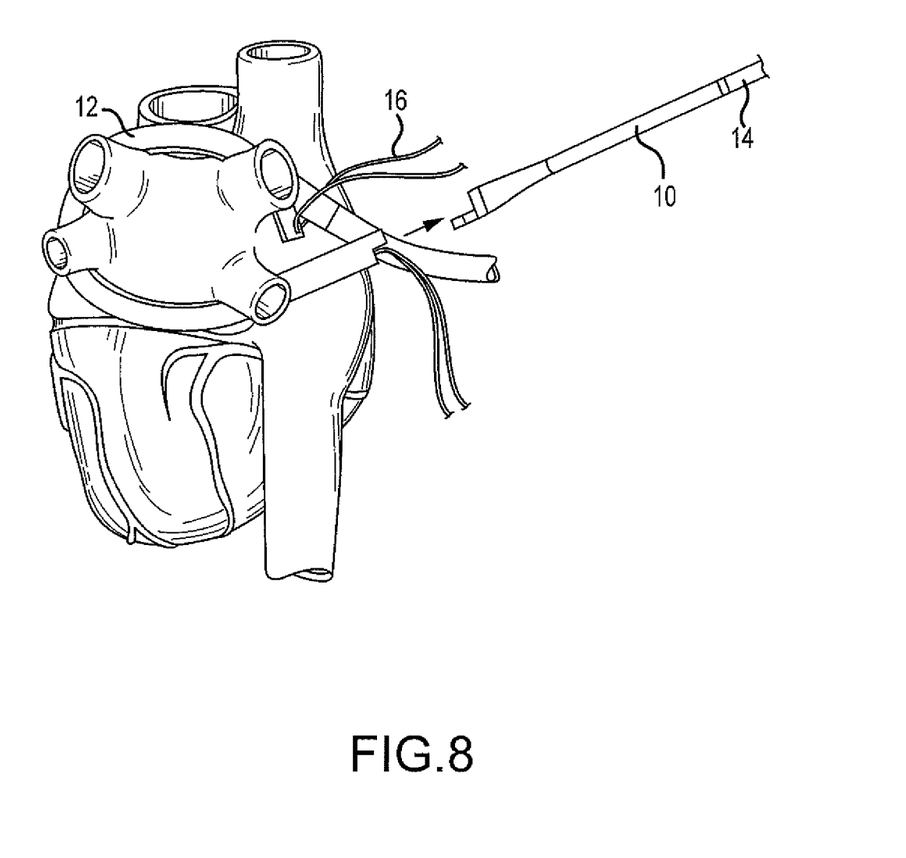
FIG. 8 illustrates a perspective view of the transition apparatus and introducer of FIG. 1 being decoupled from the ablation device of FIG. 1.

When transition apparatus 10 is used to connect device 12 to introducer 14, device 12 may thereby follow the path of introducer 14. As introducer 14 is pulled, device 12 may be positioned (e.g., wrapped) around the pulmonary veins, other portion of the heart, or other anatomical structure. Referring now to FIG. 8, once device 12 is properly positioned, introducer 14 may be detached from device 12. For example, at least a portion of apparatus 10 (to which introducer 14 may be connected) may be detached from device 12. Apparatus 10 may be configured so that the step of separating introducer 14 from device 12 is outside of a patient's body cavity, thereby making the removal step less difficult for the operator of device 12.

Figure 9:
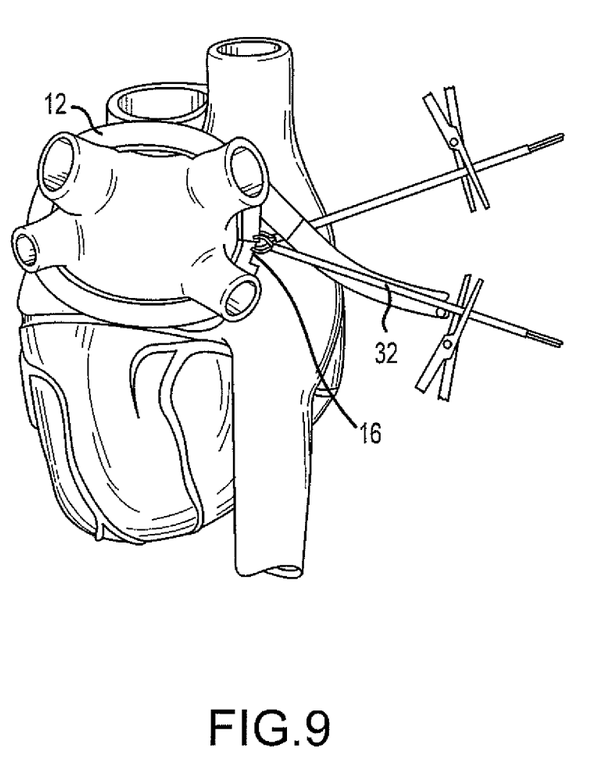
FIG. 9 illustrates a perspective view of the ablation device of FIG. 1 in place around cardiac tissue following the decoupling of the transition apparatus and introducer from the ablation device.

A method of connecting a transition apparatus 10 to an ablation device 12 having a leash 16 is also provided. The method may include providing the transition apparatus 10 having a body 20 defining a lumen for housing at least a portion of leash 16. Body 20 may have a proximal end 22 configured for releasable connection to the ablation device 12 and a distal end 24. The provided transition apparatus 10 may further include connection piece 18 connected to distal end 24 of body 20. Connection piece 18 may include a first opening or receptacle 26 configured to receive leash 16 from the lumen of body 20 and a second opening or receptacle 28 configured to receive leash 16 from first opening or receptacle 26 and direct leash 16 toward body 20. The method may further include releasably connecting the connection piece 18 to an introducer 14. The method may further include releasably connecting the proximal end 22 of body 20 to the distal end of the ablation device 12. The method may further include threading leash 16 of the ablation device 12 through first opening or receptacle 26 and threading leash 16 of the ablation device 12 through second opening or receptacle 28 so that leash 16 is directed back toward body 20. The method may further include inserting apparatus 10 and ablation device 12 into a body cavity (e.g., of a patient). After the ablation device 12 is properly placed within the body cavity, the method may further include pulling at least a portion of apparatus 10 out of the body cavity and removing apparatus 10 from the ablation device 12. In particular, the step of removing apparatus 10 from the ablation device 12 may include pulling the leash 16 (e.g., the exposed portion of leash 16) and separating the leash 16 from connection piece 18. Then, the method may include the step of using leash 16 to form the ablation device 12 into a substantially closed loop. The ablation device 12 may be formed into a loop for placement around cardiac tissue for ablation. In an embodiment, leash 16 may extend from a distal end of ablation device 12 and another leash 16 may extend from a proximal end of ablation device 12. The leashes may be connected to form the substantially closed loop. Referring now to FIG. 9, the leashes 16 extending from the distal and proximal ends of ablation device 12 may be connected by tourniquets 32 in a manner conventional in the art.

In an embodiment, leash 16 may be exposed outside of connection piece 18 and/or may extend to the side of body 20. Secondary retention member 30 may cover at least a portion of leash 16. The method may further include covering at least a portion of leash 16 with a secondary retention member 30 as described above. The method may further include removing the secondary retention member 30 (e.g., tube) prior to pulling on the portion of leash 16 that is exposed and/or extends to the side of body 20. For example, an operator may remove the secondary retention member 30, loosen leash 16, and unsnap leash 16 from the first and second openings or receptacles 26, 28. Once leashes 16 are loose, apparatus 10 may be detached from device 12. As illustrated in FIG. 8, introducer 14 may still be attached to apparatus 10 in an embodiment when apparatus 10 is detached from device 12. In other embodiments, introducer 14 may no longer be attached to apparatus 10 when apparatus 10 is detached from device 12. For example, introducer 14 may be detached first and separately from apparatus 10 when the device 12 may need to removed for additional lesion creation placement.

Although several embodiments of this invention have been described above with a certain degree of particularity, those skilled in the art could make numerous alterations to the disclosed embodiments without departing from the spirit or scope of this invention. For example, a proximal adapter may or may not be used with a carrier. All directional references (e.g., upper, lower, upward, downward, left, right, leftward, rightward, top, bottom, above, below, vertical horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A transition apparatus for use with an introducer and a medical device, the medical device having an elongate element with a first end and a second end, the first end being secured to the medical device, the elongate element defining a length, said transition apparatus comprising:
   a body defining a length and a lumen configured to selectively house at least a portion of the elongate element, wherein the length of said body is at least half of the length of the elongate element, said body comprising:
   a proximal end configured for releasable connection to the medical device; and
   a distal end; and
   a connection piece connected to said distal end of said body, said connection piece configured for releasable connection to the introducer.

2. The apparatus of claim 1, wherein said connection piece includes one or more bayonets for mating with a receptacle in said introducer.

3. The apparatus of claim 1, wherein said body consists of a flexible material.

4. The apparatus of claim 1, wherein at least a portion of said body is tapered.

5. The apparatus of claim 1, further comprising a secondary retention member.

6. The apparatus of claim 5, wherein said secondary retention member comprises a plastic part, tubing, or tape.

7. The apparatus of claim 1, wherein the connection piece comprises:
   a first opening configured to receive the elongate element from said lumen of said body; and
   a second opening configured to receive the elongate element from said first opening and direct the elongate element toward said body.

8. The apparatus of claim 7, wherein said first and second openings of said connection piece are configured to releasably retain at least a portion of the elongate element such that the portion of the elongate element is exposed outside of said connection piece when the portion of the elongate element is releasably retained in said first and second openings.

9. The apparatus of claim 7, wherein said apparatus is configured to be secured to the medical device only by retention of the elongate element in said first and second openings.

10. The apparatus of claim 7, wherein said first and second openings have a diameter less than or equal to a diameter of the elongate element.

11. A transition apparatus for use with an introducer and an epicardial ablation device, the epicardial ablation device having a leash with two ends, one end being secured to the epicardial ablation device, the leash defining a length, said transition apparatus comprising:
    a body defining a length and a lumen configured to selectively house at least a portion of the leash, wherein the length of said body is at least half of the length of the leash, said body comprising:
    a proximal end configured for releasable connection to the epicardial ablation device;
    a distal end; and
    a connection piece connected to said distal end of said body, said connection piece configured for releasable connection to the introducer and comprising:
        a first receptacle configured to receive the leash extending from said lumen of said body; and
        a second receptacle configured to receive the leash extending from said first receptacle and direct the leash toward said body;
        wherein the first receptacle and the second receptacle are configured to releasably retain the leash such that at least a portion of the leash is exposed outside of said connection piece when the leash is releasably retained in said first and second receptacles.

12. A transition apparatus for use with an introducer and a medical device, the medical device having an elongate element with two ends, one end being secured to the medical device, the elongate element defining a length, said transition apparatus comprising:
    an elongate body defining a length, wherein the length of said elongate body is at least half of the length of the elongate element, said elongate body comprising:
        a proximal end configured for releasable connection to the medical device; and
        a distal end configured for releasable connection to the introducer.

13. The apparatus of claim 12, wherein said elongate body defines a lumen that extends along the length of said elongate body.

14. The apparatus of claim 12, wherein the distal end of the transition apparatus comprises a connection piece.

15. The apparatus of claim 14, wherein said connection piece includes one or more bayonets for mating with a receptacle in said introducer.

16. The apparatus of claim 12, wherein at least a portion of said elongate body is tapered.

17. The apparatus of claim 12, wherein the elongate body defines a lumen configured to selectively house at least a portion of the elongate element.

* * * * *